United States Patent
Romano

(10) Patent No.: US 6,267,679 B1
(45) Date of Patent: Jul. 31, 2001

(54) METHOD AND APPARATUS FOR TRANSFERRING DRILLING ENERGY TO A CUTTING MEMBER

(76) Inventor: Jack W. Romano, 10701 Meridian Ave. North, Apt. 405A, Seattle, WA (US) 98133

( * ) Notice: Subject to any disclaimer, the term of this patent is extended or adjusted under 35 U.S.C. 154(b) by 0 days.

(21) Appl. No.: 09/224,557

(22) Filed: Dec. 30, 1998

Related U.S. Application Data

(60) Provisional application No. 60/070,081, filed on Dec. 31, 1997.

(51) Int. Cl.[7] .............................. F16C 1/00; E21B 17/00
(52) U.S. Cl. ........................ 464/58; 464/183; 175/320; 175/61
(58) Field of Search .............................. 464/58, 183, 174, 464/18, 77, 21, 54, 57, 61, 62, 64; 606/180, 170, 96; 175/320, 61

(56) References Cited

U.S. PATENT DOCUMENTS

| Re. 25,543 | 3/1964 | Ruegg et al. . |
|---|---|---|
| Re. 33,569 | 4/1991 | Gifford, III et al. . |
| 177,490 | 5/1876 | Fones et al. . |
| 179,747 | 7/1876 | Ward . |
| 216,858 | 6/1879 | Justi . |
| 267,343 | 11/1882 | Harbison . |
| 492,266 | 11/1893 | Browne . |
| 550,783 | 12/1895 | Elliott et al. . |
| 798,009 | 8/1905 | Buckley et al. . |
| 906,113 | 12/1908 | Curtis . |
| 1,042,760 | 10/1912 | Bradley . |
| 1,223,938 | 4/1917 | Close . |
| 1,228,439 | 6/1917 | Hotchkiss . |
| 1,232,922 | 7/1917 | Hubbs . |
| 1,429,146 | 9/1922 | Karge . |
| 1,590,666 | 6/1926 | Angell . |
| 1,630,239 | 5/1927 | Binkley et al. . |
| 1,678,335 | 7/1928 | Gaston . |
| 1,683,023 | 9/1928 | Champion . |
| 1,808,193 | 6/1931 | Webb . |
| 1,811,697 | 6/1931 | Reilly . |
| 1,812,510 | 6/1931 | Berge . |
| 1,897,542 | 2/1933 | West . |

(List continued on next page.)

FOREIGN PATENT DOCUMENTS

| 181 689 | 3/1907 | (DE) . |
|---|---|---|
| 654 418 | 12/1937 | (DE) . |
| 27 39 454 A1 | 2/1978 | (DE) . |
| 3024 413 A1 | 1/1982 | (DE) . |
| 4208221 A1 | 9/1993 | (DE) . |
| 595752 | 7/1925 | (FR) . |
| 728 739 | 4/1932 | (FR) . |
| 28115 | of 1911 | (GB) . |
| 453105 | 9/1936 | (GB) . |
| 751962 | 7/1956 | (GB) . |
| 1028327 | 5/1966 | (GB) . |
| 2015699 | 9/1979 | (GB) . |
| 502194 | 11/1954 | (IT) . |
| 42973 | 6/1926 | (NO) . |
| 617629 | 7/1978 | (RU) . |
| WO 94/09716 A1 | 5/1994 | (WO) . |

Primary Examiner—Lynne H. Browne
Assistant Examiner—Kenn Thompson
(74) Attorney, Agent, or Firm—Dowry & Associates

(57) ABSTRACT

A continuous congruent length stranded flexible Drilling Energy Transfer Member (DETM) constructed to transfer and balance action/reaction forces between an energy source and a working tip such that torque, tensile, compression and self supporting forces are constrained while the DETM operates in multiple positions of tight curvature and straight run and while translating into and out of such extremes, the balance being maintained between the extensor/torque outer configuration and an inner tensile/compressor configuration.

47 Claims, 4 Drawing Sheets

U.S. PATENT DOCUMENTS

| | | |
|---|---|---|
| 1,908,197 | 4/1933 | Webb . |
| 1,990,514 | 2/1935 | Angell . |
| 1,995,420 | 3/1935 | Fischer . |
| 2,000,997 | 5/1935 | Sharpe . |
| 2,036,528 | 4/1936 | Kesling . |
| 2,048,471 | 7/1936 | Sanford . |
| 2,235,189 | 3/1941 | Wuestner . |
| 2,255,234 | 9/1941 | Uhler . |
| 2,573,361 | 10/1951 | Rogers, Jr et al. . |
| 2,704,005 | 3/1955 | Clayson . |
| 2,747,384 | 5/1956 | Beam . |
| 2,949,753 | 8/1960 | Menoni . |
| 2,955,592 | 10/1960 | Maclean . |
| 2,958,349 | 11/1960 | McNutt . |
| 3,043,120 | 7/1962 | Waldron . |
| 3,085,406 | 4/1963 | Hanebuth . |
| 3,146,576 | 9/1964 | Welel . |
| 3,192,795 | 7/1965 | Pierce . |
| 3,242,691 | 3/1966 | Robinson et al. . |
| 3,435,905 | 4/1969 | Lazarus . |
| 3,443,451 | 5/1969 | Zieber, Jr. . |
| 3,481,156 | 12/1969 | DeCsipkes . |
| 3,552,384 | 1/1971 | Pierie et al. . |
| 3,581,523 | 6/1971 | Bartholomew . |
| 3,611,549 | 10/1971 | Pope . |
| 3,614,953 | 10/1971 | Moss . |
| 3,705,489 | 12/1972 | Smollinger . |
| 3,726,133 | 4/1973 | Morgan . |
| 3,791,898 | 2/1974 | Reml . |
| 3,852,884 | 12/1974 | Lazarus . |
| 3,906,636 | 9/1975 | Rainey et al. . |
| 3,979,896 | 9/1976 | Klett et al. . |
| 4,112,708 | 9/1978 | Fukuda . |
| 4,149,391 | 4/1979 | Driver . |
| 4,185,473 | 1/1980 | Troost ................................. 64/2 R |
| 4,265,231 | 5/1981 | Scheller, Jr. et al. . |
| 4,421,495 | 12/1983 | Kulischenko . |
| 4,424,045 | 1/1984 | Kulischenko et al. . |
| 4,445,509 | 5/1984 | Auth . |
| 4,541,423 | 9/1985 | Barber . |
| 4,589,412 | 5/1986 | Kensey . |
| 4,631,052 | 12/1986 | Kensey . |
| 4,646,738 | 3/1987 | Trott . |
| 4,655,610 | 4/1987 | Al-Jaroudl . |
| 4,664,112 | 5/1987 | Kensey . |
| 4,681,106 | 7/1987 | Kensey . |
| 4,686,982 | 8/1987 | Nash ................................. 128/305 |
| 4,690,140 | 9/1987 | Mecca . |
| 4,728,319 | 3/1988 | Masch . |
| 4,747,821 | 5/1988 | Kensey . |
| 4,771,774 | 9/1988 | Simpson et al. . |
| 4,781,186 | 11/1988 | Simpson et al. . |
| 4,790,813 | 12/1988 | Kensey . |
| 4,794,931 | 1/1989 | Yock . |
| 4,795,438 | 1/1989 | Kensey et al. . |
| 4,811,735 | 3/1989 | Nash et al. . |
| 4,917,085 | 4/1990 | Smith . |
| 4,941,466 | 7/1990 | Romano ................................. 606/80 |
| 4,979,951 | 12/1990 | Simpson . |
| 4,990,134 | 2/1991 | Auth . |
| 5,000,185 | 3/1991 | Yock . |
| 5,002,546 | 3/1991 | Romano ................................. 606/80 |
| 5,017,057 | 5/1991 | Kryger . |
| 5,041,089 | 8/1991 | Mueller et al. . |
| 5,042,984 | 8/1991 | Kensey et al. . |
| 5,049,124 | 9/1991 | Bales, Jr. . |
| 5,052,404 | 10/1991 | Hodgson ................................. 128/772 |
| 5,071,425 | 12/1991 | Gifford, III et al. . |
| 5,072,759 | 12/1991 | Moore ................................. 138/153 |
| 5,078,722 | 1/1992 | Stevens . |
| 5,084,010 | 1/1992 | Plaia et al. . |
| 5,085,662 | 2/1992 | Willard . |
| 5,087,265 | 2/1992 | Summers . |
| 5,092,873 | 3/1992 | Simpson et al. . |
| 5,100,424 | 3/1992 | Jang et al. . |
| 5,101,682 | 4/1992 | Radisch, Jr. et al. . |
| 5,102,415 | 4/1992 | Guenther et al. . |
| 5,108,411 | 4/1992 | McKenzie . |
| 5,135,531 | 8/1992 | Shiber . |
| 5,156,610 | 10/1992 | Reger . |
| 5,158,564 | 10/1992 | SchneppPesch et al. . |
| 5,165,421 | 11/1992 | Fleischhacker et al. ................................. 128/772 |
| 5,211,636 | 5/1993 | Mische . |
| 5,226,909 | 7/1993 | Evans et al. . |
| 5,239,890 | 8/1993 | Sosnoski et al. . |
| 5,250,059 | 10/1993 | Andreas et al. . |
| 5,269,785 | 12/1993 | Bonuttii . |
| 5,286,253 | 2/1994 | Fucci . |
| 5,288,270 | 2/1994 | Ishikawa . |
| 5,360,432 | 11/1994 | Shuturman . |
| 5,383,884 | 1/1995 | Summers . |
| 5,395,188 | 3/1995 | Bailey et al. . |
| 5,437,630 | 8/1995 | Daniel et al. . |
| 5,509,918 | 4/1996 | Romano ................................. 606/80 |
| 5,514,115 | 5/1996 | Frantzen et al. . |
| 5,527,326 | 6/1996 | Hermann et al. . |
| 5,562,275 | 10/1996 | Weissenflutt . |
| 5,584,843 | 12/1996 | Wulfman et al. . |
| 5,700,265 | 12/1997 | Romano ................................. 606/80 |
| 5,816,923 | 10/1998 | Milo et al. . |
| 5,820,464 | 10/1998 | Parlato ................................. 464/58 |

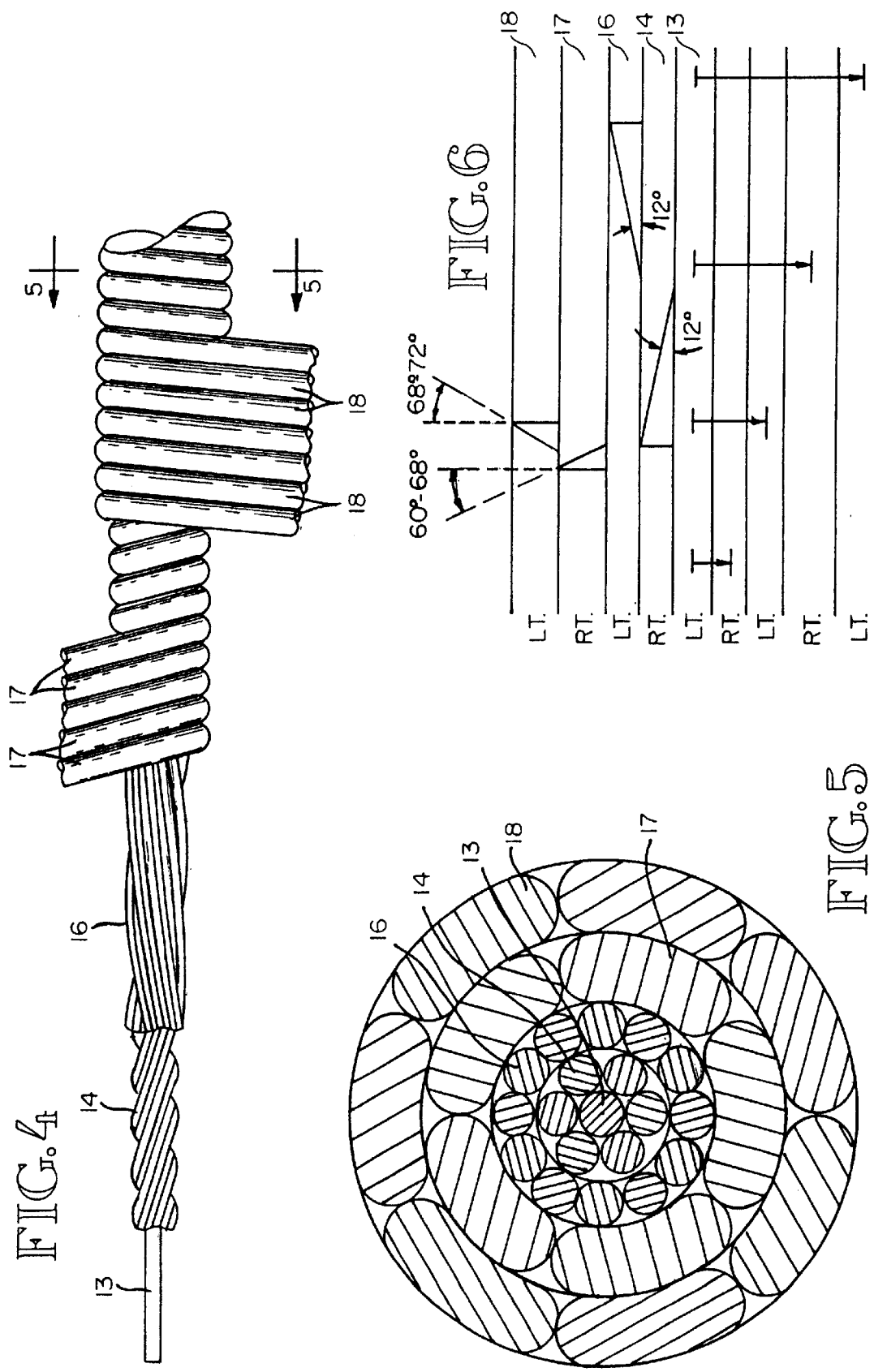

METHOD AND APPARATUS FOR TRANSFERRING DRILLING ENERGY TO A CUTTING MEMBER

This application claims benefit of Provisional Application Ser. No. 60/070,081 filed Dec. 31, 1997.

BACKGROUND OF THE INVENTION

1. Field of the Invention:

The invention relates to a method and apparatus for the transfer of rotary torque drilling energy from a power source to a drilling tip. More particularly the invention relates to method and apparatus of the character described for drilling a tight radius curved bore hole with a flexible rotary drill shaft.

2. Description of the Prior Art:

Many rotary drive apparatus exist for different particular purposes. Each flexible shaft rotary drive is designed to operate at acceptable levels for specific purposes and to accomplish operating parameters of certain specificity. None of the prior art referenced herein have been made to operate at requirements set by drilling a curved bore in a hard material. For example, most prior art reviewed and cited by applicant, although related to flexible rotary drill shafts and wire rope members, are cited for specific purposes unrelated to boring curved holes. These devices operate at very high RPMs and generally have different operating performance requirements. One such example is U.S. Pat. No. 4,686,982 to Nash which discloses a spiral wire bearing for rotating a wire drive catheter. This disclosure represents a typical type of flexible drive means which has no center core and is made to operate at very high speed, generally in excess of 20,000 RPMs. This basic design combination would fail in the drilling apparatus of the present invention due to the extreme loads encountered by the center of the present drilling energy transfer member (DETM).

Another type of prior art is a typical industrial flexible shaft configuration such as disclosed in U.S. Pat. No. 5,820,464 to Parlato which has a mandrel and six total layer wraps. These particular types of flexible shafts are made with multiple wraps of very small wires with the center comprising multiple wraps laid at a very steep helix pitch. The problem with this type of flexible shaft is that it is generally wrapped too tight and it is too stiff for the application of the present invention. Having been wrapped too tight and with a too stiff helical pitch at the center, it does not possess sufficient longitudinal strength or flexibility along the center to withstand high torque loads when passing around sharply curved radiuses.

Another such prior art example is disclosed in U.S. Pat. No. 4,185,473 to Troost. Troost discloses another example of too many lays or wraps, too many wires wrapped at too steep of a pitch angle. Also, another problem with the Troost shaft is that the pitch is too steep in the center wraps which are not laid for longitudinal linear strength along the center. This flexible shafting would also fail when put in the present operating environment since the strands are wrapped too tightly and the lack of flexibility would not allow for transmitting drilling energy around a tight curve radius. These types of flexible shafts generally have multiple wraps of wires that are substantially the same diameter and therefore are not balanced properly to handle the extreme loads experienced in multiple operating positions such as tight curves and straight operating runs.

The U.S. Pat. No. 5,052,404 to Hodgson discloses another type of torque transmitting device. This particular torque transmitter simply has too few coils and is therefor not flexible enough to withstand drilling around a tight radius. Another type of rotary transmitter is a rotary transmission conduit such as disclosed in U.S. Pat. No. 5,072,759 to Moore. The Moore transmission conduit includes an inner tubular liner comprised of polymer material and an outer layer of adhesive material. These types of devices usually comprise conduit made up of sub-assemblies of different types of wire wraps with additional component configurations. The problem with this type of devices is that the sub-assembly componentry takes up valuable space which reduces strength to below that required in a highly flexible curved drilling application. Yet another type of device is described in U.S. Pat. No. 5,165,421 to Fleischhacker et al. Fleischhaker et al discloses a lumen cable which is formed from helically wound inner and outer coils. The problem with this type of configuration is that no tensile or linear compression components exist within the structure and, as a result, failure will occur rapidly if linear stress is applied. All of these basic prior art designs would fail in the present tight radius curved bore drilling device because of the lack of balance, flexibility requirements and the extreme loads placed on the center of the DETM. Also there are balancing forces that are required in the DETM which must perform under multiple different positions during loading.

Wire rope is another type of prior art stranded configuration of some relevance. These configurations are manufactured primarily for linear travel over pulleys and are intentionally constructed so as not to rotate as they ride over a pulley. This approach teaches in the opposite direction from the present invention.

Finally my prior U.S. Pat. Nos. 5,700,265; 5,509,918; 5,002,546; and 4,941,466 represent prior art flexible shafting that has been used in a tight radius curved drilling. The problem with these rotary drives is that they do not balance the outer extensor and the inner compressor forces and hence have a reduced operating life. Their center configuration is not laid to withstand the necessary tensile loads and the outer torque layers are not wrapped for balancing the two outer lays with respect to each other and with respect to the center tensile compressor lays. Therefore, the operating life of this type of rotary drive is reduced.

General Considerations

Transmitting drilling energy along a drilling energy transfer member (DETM) between an energy source and a working tip for the purposes of drilling a tight radius curved bore presents unique operating requirements. Not only does the DETM have to operate in multiple operating positions, i.e. between curved and straight runs, it must carefully balance the net reaction forces that occur between the energy source and the multiple and variable opposing reaction forces encountered in drilling a tight radius curved bore. In general the overall work zone of the DETM includes: (1) rigid attachment at one end to a working tip; (2) travel along a short straight section; (3) travel along a tight radius curve; (4) transition from the tight radius curve to a straighter section; (5) translation up into a straighter self supporting section; and (6) then attachment to a solid power shaft. The net reaction forces of the DETM must be carefully balanced to successfully operate in these specific dynamic work zones. This includes balancing: (1) the vector forces at the cutter attachment; (2) vector forces at the transition between the cutter attachment and the curve; (3) the vector forces through the curve; (4) the vector forces at the peak stress area within the curve; (5) the vector forces at different amounts of curved radius and changing of the peaked stresses; (6) the vector forces coming off the peaked stresses and transitioning into the straight section; (7) the vector forces in the self supporting straight section; and (8) the vector forces where the DETM terminates at its attachment with a proximal solid shaft. Balance among all of the vector force relationships in the context of load sharing is also very important.

There are a number of important characteristics that must be considered when manufacturing a DETM that will operate in the aforementioned environment. Some of these important characteristics include: the number of wires; degree of cold work temper; the number of wires per wrap; the optimum stranded pitch; the optimum operational pitch; the pitch excursion off center of mass of the wires as the DETM rotates; stress relieving the wires by heat tempering after stranding; selection of the correct wire size; selection of the correct wire size percentage relative to the overall diameter of the wire and the wrap space; percentage of space within the wrap; the percentage of the diameter relative to the radius; the transition zone; the vector force patterns in a straight near the crimp; the vector force patterns in the curve at the peaked radial position; the vector force pattern excursion flexibility during transition; the vector force pattern at the laser weld straight at the end of the curve; the strand excursion side-to-side; the radial excursion; the wrap excursion between layers; the difference of excursion at the three o'clock, six o'clock, nine o'clock and twelve o'clock positions of rotation. Other considerations that must be made relate to: the peak stress areas; the laser weld termination of flexibility area; the heat affected zone control area of the laser weld; the peak in the curve; the translation of the peak drilling stresses as a DETM translates into a greater portion of a curved position and then back to the peak stresses in a straight unsupported position; and the peak forces at the proximal rigid terminal end at the crimp.

SUMMARY OF THE INVENTION

The present invention provides a flexible drilling shaft and method of constructing the same which balances the net action/reaction forces that occur between the drilling energy source and a working tip, especially when drilling in a tight radius in extremely hard or dense material. Balance is maintained as the shaft operates between and through curved and straight runs in forming a tight radius bore. A center or core load cell provides tensile and compressive strength and comprises a plurality of strands that are sized and laid at helical angles sufficient for transmitting predetermined axial loads under rotary drilling pressure. An outer wrap load cell provides torque and rotational strength and comprises a plurality of strands that are sized and laid over the core at helical angels sufficient for transmitting predetermined torque loads under rotary drilling pressure. The force fields and mass distribution of the core and outer wrap load cells are functionally balanced such that the core load cell structurally supports the outer wrap load cell against destructive axially directed forces and the outer wrap load cell structurally supports the core against destructive rotationally directed torque forces and maintains longitudinal support therefor.

In a preferred embodiment having a 0.045 inch flexible drilling shaft designed for drilling ¼ inch curved radius bore holes in such hard material as bone, a shaft configuration of 1×19+5+7 is provided. The flex shaft is constructed by first laying six wire strands in a right hand direction about a single wire mandrel and then laying a twelve strand wire wrap at the same helical angle in the opposite direction to form a first or core load cell. These strands are laid generally axially at a relatively flat helical angle of from 10°–15° for the purpose of transmitting tension and compression loads during rotary drilling. A second load cell is formed about the core and comprises a five strand right hand wrap and a seven strand left hand wrap laid at 60°–68° and 68°–72° respectively and serves to transmit torque loads during rotary drilling. The core load cell and the outer wrap load cell are functionally balanced with respect to mass and the forces contained within the flexible shaft, providing superior axial strength with the torque carrying wraps maintaining overall structural integrity of the shaft during tight radius curved bore forming.

An improved attaching means for rigidly connecting the distal end of the flex shaft to a cutter head is provided comprising, in a first embodiment, a hollow stem on the cutter head having a diameter adapted to receive the shaft end. The shaft end is then laser welded or otherwise fusibly connected to the stem to provide the rigid connection. In a second embodiment the cutter head stem is equal in diameter with the shaft end and a separate sleeve is provided to span the abutted stem and shaft ends. In this embodiment welding may be accomplished on one end of the sleeve adjacent the cutter head, providing an undisturbed bearing surface for contact with a drill guide.

BRIEF DESCRIPTION OF THE DRAWINGS

FIG. 4 is a partially cut-away elevational view of a flexible drill shaft according to the present invention illustrating the center core with alternate right and left hand lays with relatively small or flat helical angles and the outer right and left hand lays with relatively steep helical angles;

FIG. 5 is a cross sectional view taken along lines 5—5 of FIG. 4;

FIG. 6 is diagram illustrating the helical angles of the core and outer wrap strands and the moment lever arms for the several wraps;

DETAILED DESCRIPTION OF THE PREFERRED EMBODIMENT

Figure 1:
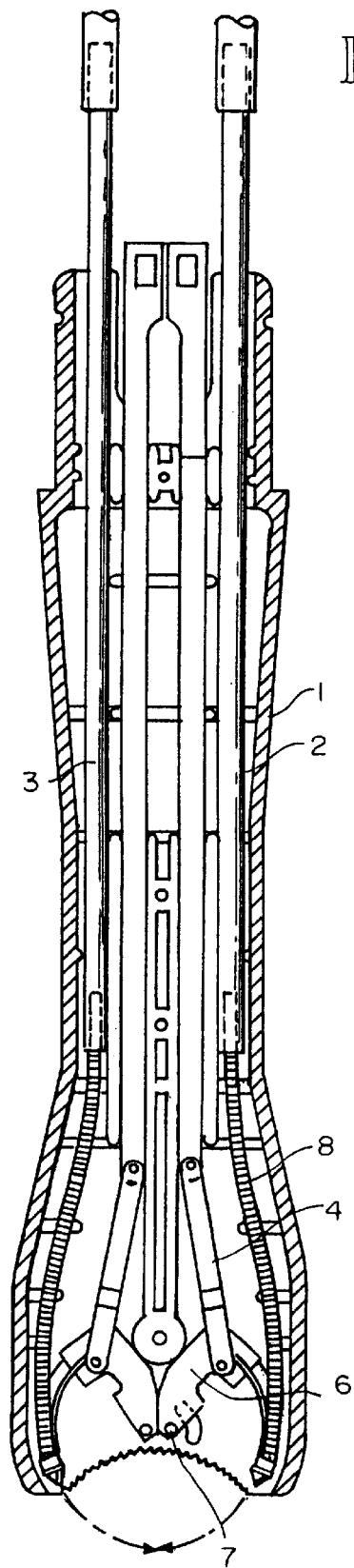
FIG. 1 is a plan view of a removable cartridge for mounting and operating two tight radius flexible shaft DETM's.
Figure 2:
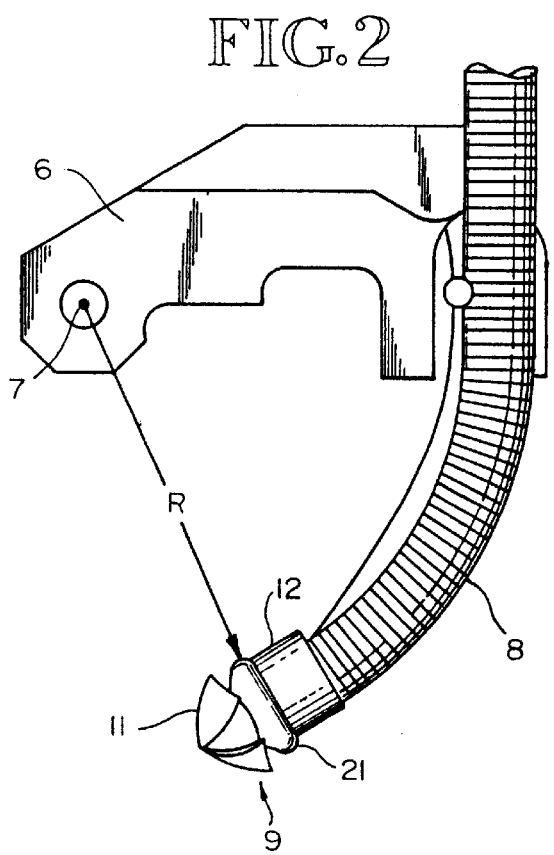
FIG. 2 is a plan view of one of the two opposed curved cutter guides and flexible drill shafts of FIG. 1.
Figure 3:
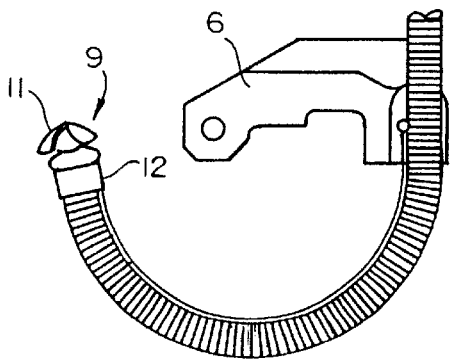
FIG. 3 is plan view of a curved cutter guide and flexible drill shaft in full extended position adapted for 180° curved bore hole drilling.

FIGS. 1–3 illustrate one prior art application for flexible drill shafts for tight radius boring. The illustrated example may be understood in more detail with reference to my issued U.S. Pat. No. 5,509,918, incorporated herein by reference and made a part of this disclosure. This prior patent relates to an apparatus for curved bore drilling utilizing a removable cartridge for mounting, actuating and guiding flexible drill shafts through a tight radius curve. FIG. 1 herein is a plan view of the removable cartridge with one-half of the two-part housing removed to show the relationship of the working parts. The housing 1 supports the rotatable and linearly slidable right and left hand rigid drive shafts 2 and 3. The drive shafts 2 and 3, the associated operating linkages, guides and flexible shafts are identical mirror images and hence only one flex shaft arrangement will be described. It will be understood that the shafts 2 and 3 in this case would be driven by some form of motor means.

With the shaft 2 rotating, a suitable articulated push-pull linkage 4 is operated to advance the flex shaft 8 from the position shown in FIG. 1 about a tight radius curve to the position shown in FIG. 2. Although the FIGS. 1 and 2 embodiment depict a double flex shaft arrangement, wherein each flex shaft and cutter tip are advanced through only 90° to form the 180° curved bore, FIG. 3 illustrates a similar embodiment wherein the cutting tip and flex shaft travel through a full 180° arc. The cutting tips for both the FIG. 2 and FIG. 3 embodiments may be identical and will normally comprise a cutting bit indicated generally at 9 which includes a sharpened and fluted cutting head 11 joined to a rear stem 12 which is in turn secured to the end of the flexible shaft 8 by means such as laser spot welding. For purpose of the present invention it will be noted that the radius R shown in FIG. 2 of the curved bore is in the neighborhood of ¼ inch.

FIG. 4 illustrates the preferred embodiment of the DETM and the method of construction or laying down the plurality of wire wraps which form the flexible shaft. The preferred construction in terms of the various wraps is characterized in the art as being 1×19+5+7 where the 1×19 center core comprises a single strand mandrel 13, six strands 14 wrapped in a right hand direction and twelve strands 16 laid in the opposite or left hand direction. The 1×19 core wires are laid down in very small or flat helical angle in the order of 12° in the illustrated embodiment but which may be varied from 10°–15°. The wraps are sloped in opposite directions as shown in FIG. 5, providing axial strength, flexibility and the prevention of elongation of the center core during drilling operation in a tight radius. The outer load cell or torque carrying wraps comprise five strands 17 laid in a right hand direction and seven strands 18 laid in a left hand direction. As shown in FIG. 6, the strands in 17 are laid at a helical angle of from 60°–68° and the strands 18 are laid at an angle of 68°–72° in the opposite direction. FIG. 5 is a cross sectional view of the assembled flex shaft showing the single wire mandrel 13, the first right hand wrap of wires 14 and the left hand wrap of wires 16. In the preferred embodiment, the mandrel 13, first layer 14, and second layer 16, may all comprise a plurality of generally 0.0045 inch diameter wires. The outer right hand five strand wrap of wires 17 may comprise 0.0065 inch diameter wires and the outer seven left hand lay wires 18 may comprise 0.006 inch diameter wires.

Figure 7:
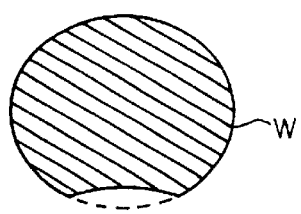
FIG. 7 is an exaggerated cross sectional view of a single strand with a land flat created by tight winding of adjacent layers of wires.
Figure 8:
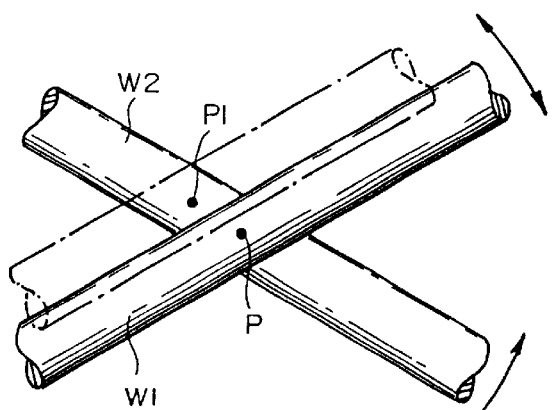
FIG. 8 is a schematic illustration of the excursion of the cross angle of the wires of adjacent wraps during rotation of the DETM in a curved bore.

FIG. 7 is an exaggerated cross sectional view of a wire W illustrating a slight deformation or "egg shape" with a "land flat" that is created on the inside surface of a wire by pressure of one wire being tightly wrapped on or across another during stranding of the flex shaft. During a non-flexing mode of the shaft, a given cross angle of successive wrapped wires will obtain with the land flats in a particular position. As the flex shaft is moved through a curved path during rotation, an excursion or change of the cross angle of the adjacent wraps will occur with the land flat ideally providing the pivot point P for the changing angle as illustrated in FIG. 8. The further from the center of the DETM, of course, the more excursion of the cross angle between successive layers of wires. FIG. 8 also illustrates the shifting of the pivot point to a second location $P_1$ which will occur if the pitch angle is not properly controlled, the effects of which will be presently described in detail.

Figure 9:
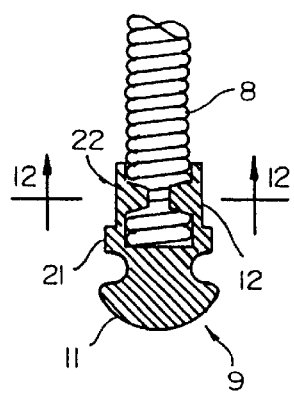
FIG. 9 is a partially sectioned elevation of a flex shaft secured by laser welding within the stem socket of a cutting member.
Figure 10:
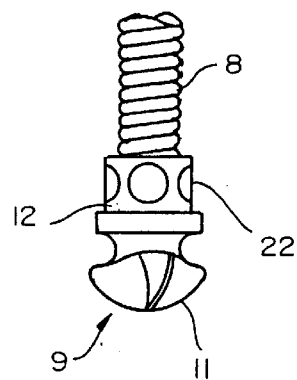
FIG. 10 is an elevational view of the FIG. 9 flex shaft and cutting tip with laser welds.
Figure 11:
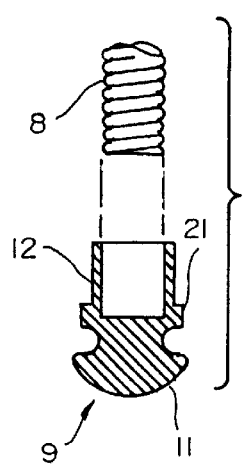
FIG. 11 is an exploded view of the FIG. 9 flex shaft and cutting tip.
Figure 12:
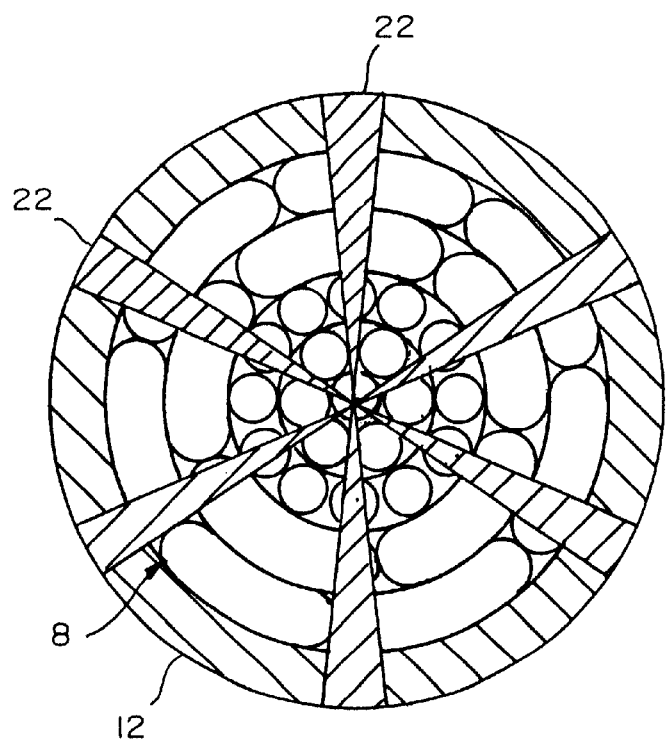
FIG. 12 is a cross sectional view taken along lines 12—12 of FIG. 9 illustrating laser weld penetration.

FIGS. 9–12 illustrate methods for attaching the end of the flexible shaft 8 to a working tip 9. As seen in FIGS. 9–11, the cutting head 11 is joined to a cylindrical stem 12 with a shoulder 21 located therebetween defining an area for the cutting member to engage the curved guide means 6 of the drill apparatus. The stem 12 may constitute a bearing area engaged with the end of the guide means 6 of the drill apparatus. The stem 12 also has an internal socket into which the end of the flexible shaft 8 is received, as illustrated in FIG. 9. The end of the shaft 8 may be laser welded or otherwise fusibly joined as at 22 to solidly connect the cutter bit 11 to the flex shaft 8. As illustrated in FIG. 12, the laser weld or other fusing operation must penetrate to the center of the flexible shaft, in this instance to the mandrel 13. As illustrated, the laser welding is directed transversely at the exterior of the stem 12 to achieve the desired penetration. In the alternative, the laser weld may be directed obliquely onto a non-bearing area of the cutter 9 such as against the shoulder 21 at two or more locations at the end of the flex shaft without unduly affecting the cylindrical shape of the stem 12 at the bearing point.

Figure 11A:
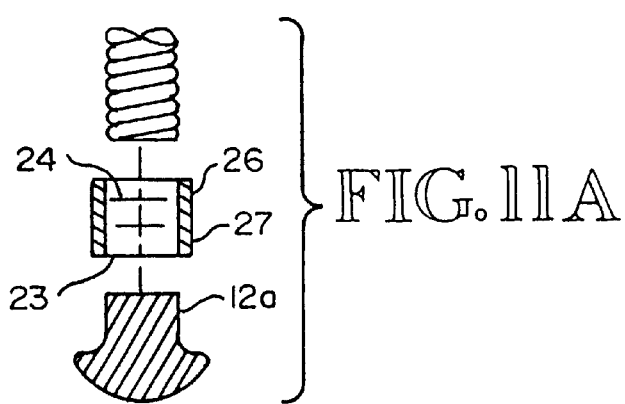
FIG. 11A is an exploded view of a modified structure for attaching the shaft to a cutting tip.
Figure 11B:
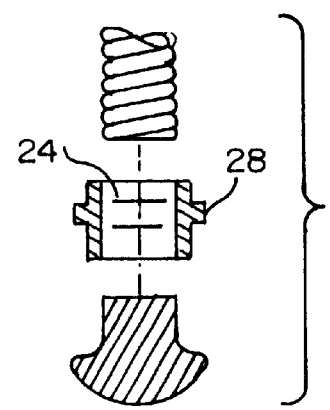
FIG. 11B is an exploded view of the 11A attaching means provided with a shoulder element.

An alternative means of attachment between the flexible shaft 8 and the cutter 9 is to form the stem of the cutter with a diameter no greater than the diameter of the flexible shaft 8 as shown at 12a in FIG. 11A and 11B. A separate sleeve 23 is then fitted over the stem 12a and over the adjacent end of the flex shaft 8. The stem 12a and the end of the flex shaft 8 can then be secured to the sleeve 23 such as by laser welding. It is preferred that the flex shaft 8 fit within the sleeve 23 sufficiently such that it can be spot welded within the sleeve at a point spaced from the bearing area of the drill guide. The sleeve 23 may also be formed with a flange or shoulder 28 as shown in FIG. 11B for contacting the drill guide. As illustrated in FIGS. 11A and 11B, the end of the shaft 8 and the stem 12a of the cutter are engaged at a position indicated by the line 24. With this arrangement, the area 26 above the line 24 may be used for welding, leaving the area 27 below the line as a clear bearing area for the drill guide. In the alternative, the curved guide of the drilling cartridge may be provided with a counterbore shoulder to abut the sleeve bottom and thereby eliminate the need for the shoulder. One reason for the concern with respect to the flange 28 is the overall diameter of the cutting tip in any attaching mechanism is that space must be provided for passage of the material being bored e.g. chip removal in the case of a curved bore formed in a hard material.

Generally speaking a DETM according to the present invention has multiple complex force balance mass requirements. The control and balance of the work energy that the DETM transfers is that required to constrain and confine the action/reaction forces between the energy source and the working tip. The control and balancing of the work energy that is done by the DETM is expressed in terms of successful function, the balances are also expressed with respect to function. Balance and function are expressed in terms of mass. Leverage position is expressed as moment lever ratio with respect to distance from the center of the DETM.

Moment lever combination also relates to the amount of tensile strength in balance with the amount of rotational strength. The overall tensile strength is found within the center core. The overall rotational strength is found between the balance of the outer wraps of the DETM.

Mass

For the purposes of this application the term "mass" shall mean the quantity of strand material for any given length. The 1×19+5+7 DETM comprises two primary, three secondary and four tertiary load cells. Constrained within the center of this is the center mandrel wire. The two primary load cells comprise a core or inner tensile/compressor cell, 1×19, comprising 41.6% of the total mass and the outer torque carrying load cell +5+7 comprising 57.3% of the total mass. The three secondary load cells comprise the initial 1×9 inner, tensile ell comprising 41.6% of the mass; the +5 right hand laid load cell which comprises 25.1% of the total mass; and a +7 left hand lay load cell comprising 32.2% of the mass. The four tertiary load cells comprise a +6 right hand lay comprising 12.6% of the mass; a +12 left hand lay comprising 27% of the total mass; a +5 right hand lay comprising 25% of the total mass; and a +7 left hand lay comprising approximately 31.3% of the total mass. The central mandrel wire comprises approximately 1.8% of the total mass. It is to be understood that the mass percentage quantities may vary plus or minus 5% with the scope of the present invention.

Slope Relations

Each of the two primary, three secondary and four tertiary load cells are wrapped with a helical slope angle. In comprising the two primary load cells the 1×19 center tensile load cell comprises the sum of the central mandrel plus the +6 right plus the +12 left. The sum of the slopes of the helixes for the 1×19 inner tensile is 8.8× directed towards the linear tensile/compressor slope of the 1×19 center strand. The sum of the helical slopes for the +5, +7 outer torque equals 4.3× directed to the torque. In other words inner helical tensile 1×19 center core comprises a +6 right with a preferred helical slope of approximately 12° with a range of 10°–15° wrapped against a +12 left helical preferred slope of approximately 12° with a range of 10°–15°. The +6 right 12° slope is helically directed to a factor of 4.6× towards tensile the +12 left 12° slope helically directed to a factor of 4.2× towards tensile. The +5 right hand lay slope ranging from 60°–68° has a slope which is helically directed to a factor of approximately 2.3× to torque. The +7 left hand lay approximately 68°–72° has a slope which is helically directed to a factor of approximately 2× toward torque. Therefor, the sum of the helical slopes for the center tensile core of the 1×19 is approximately 8.8× directed towards the helical tensile slope. This balanced with respect to the sum of the helical slopes for torque comprising a factor of approximately 4.3× directed to helical torque. To summarize, the DETM includes; +6 right comprising a 4.6× helical slope directed towards tensile over torque, the +12 left comprising approximately 4.2× of a left helical slope directed towards tensile over torque, +5 right comprising approximately 2.3× right helical slope directed for torque over tensile, and a +7 left comprising approximately a factor of 2× left helical slope directed towards torque over tensile.

Moment Arm Relationship

The moment arm lever is defined as the distance from the center of mass of the central mandrel wire outwardly to the center of mass of each of the +6, +12, +5 and +7 load cells. Each of the moment lever arms comprises approximately an equal additional distance going from the center to the outer wrap. For example the +6 right moment lever distance, meaning the center of mass of the mandrel wire to the center of mass of the +6 right, is approximately 25% of the total distance. The center of mass of the central mandrel wire to the center of mass of the +12 left lays approximately another 25%. The center of mass of the central mandrel wire to the center of the mass of the +5 right is an additional approximately 25% and the center of mass of the central mandrel wire to the center of mass of the +7 left is another approximately 25%. Therefor, the moment lever from the central mandrel wire to the center of mass of the +6 right is a factor of 1× or 25% of the total, and the moment lever arm of the +12 left from the center mandrel wire to the center of mass of the +12 left is approximately a factor of 2× or 50% to the total. The moment lever arm of the +5 right or the distance from the center mandrel wire to the center of mass of the +5 right is approximately 75% or a factor of 3× to the total. The moment lever arm of the +7 left or the distance from the center mandrel wire to the center of mass of the +7 left is approximately 100% or a factor of 4× to the total. It is understood that the total moment lever arm from the center mandrel wire to the center of mass of the 7 left is approximately 100% or a factor of 4×.

Cross Sectional Area

The cross sectional area of the drilling energy transfer member is also evaluated with respect to manufacturing planning and how much of the cross sectional area in the transfer member is allocated to the different load cells. In considering the DETM and the four tertiary plus the center mandrel wire, the cross sectional areas are established as follows in respect to percentage of cross sectional area with respect to the total area. The center mandrel wire comprises approximately 0.99% of the total cross sectional area; the +6 right lay comprises approximately 0.7% of the total cross sectional area; the +12 left lay comprises approximately 16.9% of the total cross sectional area; the +5 right lay cross sectional area comprises approximately 45.2% of the total cross sectional area; and the +7 left hand lay comprises 54.7% of the total cross sectional area.

Volume

Volume for the purposes of this invention relates to the amount of cubic space allocated to each particular individual work load cell which comprises the DETM. The volume, and for academic purposes only for this example, we will use a height that is 2× the diameter (or a unit measure of 9). This is derived by taking the total volume of the DETM as if it were a cylinder, and subtracting the volumes of the respective work load cells so as to arrive at the cubic volume space of each individual load cell. This is important in determination of what the actual balances will be between the load cells. The quantity of strand material allocated for and placed within these volumetric load cell spaces determine what the actual mass is and that is important to the process of the determination of balances between load cells.

With respect to the two primary, three secondary and four tertiary load cell balances, it is relevant to first state what the percentage of load cell allocation is with respect to the total of all five of the load cells. The center mandrel comprises approximately 1% of the total volume. The +6 right load cell comprises approximately 8% of the total volume. The +12 left load cell comprises approximately 16% of the total volume. The +5 right load cell comprises approximately 37% of the total volume. The +7 left load cell comprises approximately 37.7% of the total volume.

*2-Primary: The inner tensile load cell of approximately 25% of total volume balances with the outer load cell of approximately 75% of the total volume.

*3-Secondary: The inner tensile load cell of approximately 25% of the total volume balances with respect to the outer torque carrying load cell comprising a) the +5 right load cell which is approximately 37% of the total volume and b) the +7 left load cell which is approximately 37.7% of the total volume with respect to function and having one central mandrel wire.

*4-Tertiary: The four tertiary load cells are balanced each with respect to the other and balanced with respect to function and having one central mandrel wire.

Excursion

Helical pitch is expressed with respect to excursion defined as change of the cross angle of the adjacent wraps as they rotate about the center of the DETM. In the curve, and under whipping and coiling circumstances, the further from the center of the DETM, the more excursion of the cross angle. The pivot or cross angle between individual wires is important with respect to the land flat that is created on the inside surface of a wire during wrapping or stranding. Small land flats create, for lack of a better analogy, a one-sided Lincoln log stability flat. It is important that the opposing wraps that are further from the center pivot closely to the land flat pivot point. It is also important that the DETM is stress relieved or spring temper killed as close to the operating or torque loaded position as possible. It is common in manufacturing of flexible shafts having wires between 0.0045 and 0.008 inch diameter to have gaps between wires. Any such gaps between the strands in a tight radius transfer application become closed due to the great forces. As the wraps rotate in the tight radius around the center of the DETM, the wires are pulled tight and buttress up against each other side-by-side and change pitch around the rotation from the twelve o'clock to the three o'clock to the six o'clock to the nine o'clock and back to the twelve o'clock positions. Thus, since these wires buttress contact on all sides, rotation of the DETM from the outer twelve o'clock position to the inner six o'clock position causes the pitch excursion angle to open and close. This operating pitch excursion angle takes a full cycle with one complete revolution of the DETM. This excursion cycle occurs in frequency depending upon the RPM of the DETM. For example, if the DETM is rotated at 625 RPM, these excursion angles change at a central pivot point on the land flat 625 times per minute. This creates a cyclic operating pitch excursion load on the DETM. One of the most distinguishing characteristics of the tight radius DETM application is the degree of excursion that is necessary between the wires relative to other standard applications. For example, industry standard flexible shafts are made generally to operate at a radius of about 3 inches with a 0.045 inch diameter DETM. The tight radius flexible shaft application of the present invention and the present operating environment is into and out of a radius of approximately ¼ inch or 0.25 inches. This represents a radius that is approximately 8 to 10 times smaller than the average flexible shaft operating radius. With this radius, the wires laid within the transfer member make an excursion rate that is approximately 800 to 1000 percent more than the standard DETM.

It is because of the greater amount of excursion required in the tight radius drilling application, as well as the requirement that the DETM must constrain the drilling energy in a straight unsupported mode, that the balances need to be controlled in new and unique ways. This larger amount of excursion also requires important coordination during manufacturing, e.g. maintenance of the proper pitch as stranded, proper wire size and proper wire size per layer. Also, the proper balances in pitch and the spring stress relief tempering or heat treating of the DETM after its completion must be controlled such that the adjusted operating pitch, the adjusted operating angle excursion and the land flats all match up in a manner that the pitch excursion angle of the two outer wraps maintain alignment such that the flats act as cross pivot points for the operating pitch excursion.

In the preferred embodiment of the 1×19+5+7 DETM described, excursion occurs between all wires and between all wraps. It is important to note that the cold work temper of the wires, number of wires in each lay, the slope of the helix in each lay and the wire diameters in each lay all play an important role in balancing and stress control and the cold working during operation of the mass of this construction for the successful operation of constraining the action/reaction forces encountered by the DETM in operation throughout the plurality of different operating positions described. One of the most unique requirements encountered by the DETM in this application is that the peak forces encountered along the curve increase and decrease with the actuation of the advancement and retraction of a curved drill guide. This means that these force couplings and balances slidably translate linearly along a portion of the DETM which must trade off the force parameter requirements back and forth and up and down along its length in association with the actuation of the curved drill guide. Reference is made to the unique requirements found with respect to the applicant's prior issued patents cited above.

The angle of operating pitch excursion is especially important in the outer seven left lay and the middle right five lay wraps. It is in this balance that the center of the land flats act as a pivot for this excursion, thus making it important that the manufacturing pitches and the helical slope of the wires are stress relieved and spring temper killed at pitches that are as close to the operating excursion pitch as can possibly be controlled. This keeps any circular cyclical rubbing or galling at the land flat area and keeps the outside diameter of the wire uniform during operating pitch excursion. If there is too much circular operational pitch excursion at the land flat area, then the wire can ride up the sides of the land flat, changing the diameter of the overall DETM. This is also important since the land flat pivot point may act as a microfulcrum. When the wire land flats, the operational helical pitch excursion angles and the temper stress relief in the center of mass balances are not matched up at the manufacturing phase, there is no operational harmony in the transfer member and the molecular tempered material's center of mass is agitated to cause microfulcrum cold work and early fatigue. When the operational pitch excursion is incorrect the excursion between the left hand lay outer and the right hand lay middle wire takes the form of a circular pattern rather than a pivotal pattern. It is the circular pattern that causes the outside diameter changes during the circular galling and impingement pattern. It is the circular motion pattern that causes the excess microfulcrum stresses on each wire as the opposing wires are fulcrum bent with each rotation as the wires hit resistance on the sides of the land flat area.

Manufacture

The key considerations in the manufacturing process are: the drawing of the individual wires for size; drawing of the individual wire size to a desired temper along with the successive reduction and annealing; the rate for drawing the wire; the percentage of downsizing at each draw; and to arrive at the desired KSI for each wire. The proper KSI temper is important relative to the DETM being able to withstand the appropriate shock and vibration for the application. It is also important for the KSI temper to be drawn relative to overall load sharing and local energy efficient strand motion spring rate excursion and operating pitch excursion. The wires are drawn and pulled through drawing dies with a lubricant to facilitate smooth drawing. This lubrication provides sufficient surface treatment between the wires such that excess galling and destructive surface fretting does not occur. Stress relieving is heat treat tempering which is important at the end of the manufacturing process in order to relax the wire and take the spring loaded tension out of the transfer member resulting from the multiple cold working of the material during manufacturing. Cold working of the material occurs at both the wire drawing stages and stranding stage. Spring load tension is built up in the wires from stranding. It is the stress relieving or heat treat tempering that tempers the wires such that when a wire section is cut it will maintain its diameter and resist uncoiling. The center of mass of each wire has been established and set by the stress relieving and heat tempering.

Small wires ranging in sizes from 0.0045 inches and smaller to 0.0081 inches and larger are commonly drawn down to desired wire diameters by being drawn through diamond dies. Common considerations in the wire drawing process include the rate of reduction per draw that should be made, and how that rate of draw is managed to produce a wire of a certain desired tensile strength. Different materials are drawn at different draw rates for different desired specifications and wire sizes. For example, for the stainless steel alloys of 304 SS, L605SS and MP35N stainless steels, the desired ranges of tensile strength hardnesses may be drawn differently to obtain average ranges for a desired specification. For the 304 stainless steel an average tensile draw hardness would be approximately 330 KSI. For the L605 alloy, an average tensile draw hardness would be approximately 190 KSI. For the stainless steel alloy MP35N, an average tensile draw hardness would be approximately 290 KSI.

The wires are drawn according to a certain pattern percentage of reduction in diameter by the diamond dies and then annealed in preparation for softening the material to take another cold work reduction in diameter. This drawing and annealing is alternated and coordinated until such wire is at the final diameter having the desired tensile strength. The tensile strength ranges may be controlled, and coordinated with flexibility regarding the final tensile strength and can vary quite widely, up to 30% in either direction, to have either a higher or lower tensile strength.

Mass and Force Balancing

Drilling tight radius curved bores wherein the flexible shaft operates and travels within the confines of the curved bore for which it provides drilling energy presents new operating conditions, new physical demand requirements and difficult engineering challenges. These new DETM challenges include maintenance of structural integrity for increasing operating life cycle and a radius of curvature which can be up to 1200 percent tighter than normally found in industry for a particular transfer member diameter. Also, curved boring in a hard material generates high torque loads which are compounded by drilling pressures, friction, chip cycling or peck drilling along a curved path, bending and straightening, chip packing and material debris removal, cyclic loading at a rate relative to the number of RPM's, cyclic loading at the rate of chip cycling or peck drilling along the curved path, over stressing, uneven materials and other elements of stress. The size of the DETM is limited to fitting in the curved bore along with a curved guide means and working tip means. The DETM must also be adapted to attach to a cutting means in a configuration which must operate successfully within the confines of a curved bore space. The diameter of the DETM must also be smaller than the cutting tip and the size of the bore that is formed. The cross section of the flexible shaft is also limited as a result of having to share space in the curved tunnel with the curved guide.

The tight radius under which this new DETM operates, along with its outside diameter limitations and high helical shear torque loads, present extreme unique tensile support and astringent engineering and design requirements that are not found in other flexible shaft applications. This means that the specific design configuration and the structural composition of a tight radius DETM must be optimized by balancing the mass and the forces contained within the transfer member to a functional output. The method of optimizing the transfer member's structural configuration according to the present invention was discovered by studying the microscopic failure mode of many different flexible member configurations. The failures concerned occurred as a result of operating under the strain of drilling a tight radiused curved bore at radiuses which can be up to 1200 percent tighter than normally found in association with the prior art.

A flexible member having multiple layers wherein each layer comprises a plurality of strands has been tested and evaluated for performance in an apparatus for drilling tight radius curved bores. This curved bore drilling apparatus provided the specific conditions and operational demands under which to demonstrate the criteria for a flexible DETM that would operate under these conditions. From this failure mode analysis, it was observed from the many different types of flexible shaft constructions tested that the primary mechanism of injury or failure process observed was a lack of strength and force capacity balance between the center core of the flexible shaft and its outer torque carrying section. These two primary operating load cells were unbalanced in that the center of the flexible member would fail initially under the extreme axial loads. This resulted in a construction break down and a reduced cycle life. The center core of up to approximately 50 percent of the cross sectional center dimension or approximately 0.018 inches to 0.025 inches of a 0.045 inch outside diameter flexible member will break first towards the center, eliminating the internal support. Without the internal support, the outer torque carrying wraps are left with no inner tensile or compressor support. This leads to the middle right hand layer elongating followed by a reduction in the overall diameter of the transfer member causing narrowing. The outer most layer then elongates, straightens, collapses and then the entire DETM would fail. Thus the mechanical structure breaks down and loses the advantage it has by the size of its outside diameter resulting in complete loss of its structural integrity resulting in fatigue and failure. This happens quickly once the center is fatigued. Maintenance of the configuration, construction and structural position of the strands in the DETM during operation became the engineering challenge in this curved bore application.

Therefore, it is important to relate balance in the operating life of the mass between multiple complex load sharing, load carrying, load cells. The essence of balancing these forces with respect to function output is that the operating life cycle of the transfer member is increased. Without balancing properly these force/mass relationships, each with respect to the other, the mechanical structure breaks down, loses the advantage it has by the size of its outside diameter resulting in a complete loss of its structural integrity and resulting in fatigue and failure. The present invention solves the problem of balancing many complex load carrying cells to function output and to eliminate initial breakage and failure due to weak tensile axial strength toward the center of the flex shaft. A flexible strand construction was concerned in which the first failure mode area of the construction (breakage of the center which can have up to 50 percent of the cross-sectional measurement in the center) has superior tensile axial strength and is balanced to the outer torque carrying portion of the transfer member. The inventive concept contemplates a flexible shaft wherein the center core of the construction is laid primarily axially and longitudinally for superior tensile and compressive properties, thus holding up to the extreme longitudinal stresses encountered by the center core during torque and rotation in tight radius curved bore drilling. This invention constrains the drilling energy of the net action/reaction forces that it encounters between the energy source and the working tip. This invention also withstands the drilling forces acting back onto itself and holds the structural configuration of the DETM together during tight radius curved bore forming. Without a center core configuration constructed and laid axially to optimize the tensile axial strength of the center of the flex shaft and to hold the core balanced with the forces enacted for the primary rotary stresses, the overall life cycle is substantially reduced sometimes up to 200–400 percent. It has been determined that use of L605 stainless steel in the two outermost rotational helical torque carrying wraps would inherently provide sufficient strength to withstand the extreme pressures and the extreme stresses of drilling tight radiused curved bores, if the configuration of the center strands were optimized to balance the axial loads with their rotational torque loads. Building up the axial tensile/compressive properties of the center of the flex shaft to a level that is balanced in function to the outer torque carrying wraps was discovered to be a solution to maintaining the overall construction integrity of the transfer member during tight radius curved bore forming.

When the flexible DETM encounters extreme tight radius torque and pull forces, each strand of the flexible shaft must work with the remaining strands to share its particular load requirement during rotation while withstanding drilling energy stresses. When one strand fails, the entire construction falls apart like a domino effect, starting with the first failure and going on to the other strands until the entire flex shaft has collapsed under the load. This failure happens quickly.

In addition to the above considerations, joining methods for flexible shafts that travel within the confines of a curved bore are extremely limited by their size and shape, having severe space limitations. The length of the transfer member portion which is available for joining to a cutting tip is generally not much longer than its diameter. Therefore a 0.045 outside diameter transfer member has a length available for joining to a working tip of not much more than 0.045 or approximately 0.050 at one end. This means that the flex shaft strands must be held together along a cross section so that the flex shaft acts as a solid unit in cross section in unity with the working tip, where it is joined to the working tip, in order to withstand the extreme forces incurred at the junction where it ceases to become flexible and becomes a solid integration with the working tip. End point forces at this junction are extremely high and are finely focused such that the transfer member goes from flexible to rigid in a very short section. The methods of joining used here are put to an extreme structural test, once again given the spacial size and shape limitations required in order to travel within the confines of the curved bore for which it provides energy. Just one of these limitations is that this joining area must be short enough in linear length such that it will travel into and out of the curved bore. Therefore a flexible shaft must have strands, layers and cross-sections which are joinable one to the other and joinable to a cutting tip. The end section must be capable of acting as a solid cross sectional unit across the cross-section at the junction where it attaches to a boring tip. This section where the flex shaft flexibility ends in the connection point to the boring tip endures extremely high end point torque and pull forces. If the strands of the flex shaft are not held together as a unit, the strand will become disassociated and unravel causing a loss of structural unity and failure under the extreme loads of forming a tight radius curved bore.

The provisions of a flexible DETM that is properly balanced in load force, one wrap with respect to the other, and having axial load properties in the center of the overall construction primarily balanced with the outer torque carrying wraps, was determined to be the solution to the problem of early breakage. Failure mode analysis by microscopic observation of the many different flexible shaft constructions which were put under the loads of drilling a tight radius curved bore was conducted and observed. The configurations which were not constructed to have the proper load cell force mass balances one with respect to the other failed earlier. The configurations which were not constructed to balance the center core to the outer torque carrying wraps failed early. The configurations which were not constructed to have a center core that had been manufactured to withstand the extreme axial center forces found in tight radius curved bore forming failed at a rate that was 200 to 400 percent earlier than the present invention.

More specifically in a 0.045 diameter transfer member the center approximately 50 percent of the shaft, or approximately the center 0.020 inches, comprises a plurality of strands that are constructed to provide axial strength. These strands are laid more axially or in a longitudinal fashion more parallel to the long axis of the flex shaft. These longitudinal wraps have less wraps per inch than conventional flex shaft centers, and being laid longitudinal to the axis of the flex shaft, and closer to the center these strands provide flexibility and the necessary compression strength to support the outer wraps so as to hold their structural position during operation. This is contrary to and teaches opposite of the construction found in a conventional flex shaft which has multiple coil spring-like layers comprising the center approximately 50 percent of the shaft. The tensile strength characteristics of this new center construction specifically reduces elongation, provides flexibility and leads to the maintenance of the structural positional construction of the outer torque carrying wraps. This leads to maintenance of the overall construction integrity for a much longer life cycle. The maintenance of structural position of each wire during operation adds significantly to the operating life of the transfer member in a tight curved bore forming apparatus. The extreme axial load placed on the center of the 0.045 inch outside diameter flex shaft operating at a 0.25 inch radius cutting a 2 mm diameter curved tunnel in a hard material is caused by the severe deflection of the strands as they rotate about the sharply curved center axis of the construction. This deflection occurs at a spring rate percentage that is up to approximately 1200 percent greater than the deflection encountered in a flexible member operating at a radius of 3 inches.

Specific Embodiments

Referring to FIG. 4, a layer of approximately five strands 17 are laid around the center core in a right hand direction. This set of right hand laid strands must have a pitch that would resist opening up from shear forces in its outer arc of its rotation with the shaft in a curved position. The strands in the outer arc are extended and have the most operation pitch excursion. This open pitch angle and excursion places the strands in a pitch position that is vulnerable to taking a set in the straightening direction when torque loads are applied. It is in the outer arc that these right laid strands take a side load or sheer stress that applies forces that will tend to open them up longitudinally and straighten them out. It is the outer left wrap of seven strands 18 which tighten on the middle right lay strands 17 causing opposing work of the two outer wraps when torque loads are applied. The two outer layers wrapped in opposing directions provide interlocking forces which help constrain the overall drilling energy especially in the straight unsupported position.

In addition to the described preferred embodiment of FIGS. 4 and 5, specific constructions for flexible shafting intending to increase the tensile axial load strength of the core while balancing the multiple load carrying cells one with respect to the other include:

Example-1 a 1×7+5+7 where the wire sizes comprise, from the center to the outer, a center wire size of 0.0075 inches, middle wire size of 0.0069 inches and outer wire size of 0.006. This construction uses standard draw from 0.0075 wire. This center construction has a break load of approximately 68.4 pounds and a complete shaft construction break load of approximately 6.7 in. elongation prior to break and a break strength of about 75.7 pounds. These wires are drawn down to 0.00745 inches from 0.0085 inches thus having a normal cold work hardness.

Example-2 a 1×7+5+7 construction that has the same wire sizes and the same layers as example-1, however, the center core (1×7) of the 0.0045 inch strands has taken a higher cold work property to increase the hardness of the wire through wire drawing cold working. The center wires have been drawn down to 0.0075 inches from 0.0095 inches which increases the hardness of this center construction thus increasing the tensile break loads of this center construction. The cold working of this type of draw resulted in a 88.5 pound center break load and an overall flexible shaft break load value of 101.8 pounds with an elongation of 2.8 percent prior to break. The flex shaft configurations of Examples 1 and 2 have a high center core tensile axial break resistance, however, their stiffness requires an operating rate of curvature of approximately ½ inch.

Example-3 a 1×9+5+7 construction when comprising a central mandrel wire of 0.010 inches with eight 0.006 inch wires wrapped around this for the center core adding five right lay wires and seven left lay wires. The overall break load for this transfer member is approximately 83 pounds with an elongation of 3.3 percent prior to breakage. These reduced elongation factors show the increased axial resistance to stretching and it is the providing of these axial compression strength values that holds the two outer coil wrapped layers within their constructional positions preventing breakdown. This construction requires an approximate operating radius of 0.5 inches as a result of the stiffness of the 0.010 center mandrel and the eight wires wrapped around that.

Other strand configurations were observed to have high tensile characteristics and enough strands to have the flexibility to withstand the tight radius applications however in larger wire diameter sizes. These strands have the configurations called 7×7 and 7×19. These strands are commonly used as integral units but have not been disclosed prior hereto to be placed in the center of a DETM and to be used as the center axial compression load carrying portion of a tight radius flexible DETM or to be placed to specifically provide the axial compression strength to the center of a rotary transmission shaft. The number of strands placed in an axial lay in the center core of the construction for purposes of building the resistance to elongation in a tight radius flex shaft in a fashion so as to balance in load mass and force the function output of the outer torque carrying loads may vary, depending on the specific operating radius and diameter of the flex shaft. This is related to the specifications of the curved drill hole which is desired to be drilled. Examples of center constructions which may be used as the center of a tight radius flex shaft include 1×19, 7×7, 7×19 and any other construction which meets the requirements of providing axial compression strength, the flexibility, linear longitudinal lay and prevention of elongation and construction break down. The outer two wraps may also vary depending upon the diameter of the DETM and the tightness of the radius. If a curved drill hole with a larger radius is desired, more strands may be added to each of the two outer layers without interfering with the performance. Also a stiffer center core is suitable if a curved drill hole with a larger radius is desired. In the case of a smaller radius it may be required to reduce the number of wires in the outer wraps and increase the number of center wires stranded with more axial configurations providing more axial strength and flexibility to withstand the center axial loads which hold in balance the two outer wraps in their structural position. It is the balancing of the loads, the masses and the forces between the load carrying work cells of the DETM one with respect to the other which is the subject of the present invention and the preferred embodiment of the 1×19+5+7 transfer member configuration disclosed herein. It will be apparent to those skilled in the art that these construction balances may be adjusted for varying ranges of tight radius curved bore requirements. For example, adjustments may be made regarding the principles of balancing of the forces and masses of the load carrying cells when a radius larger than 0.25 inches is desired. The converse is true when a radius smaller than 0.25 inches is desired. These two principles apply in connection with the desire to drill the same 2 mm curved drill hole. Also the balances between torque and axial load flexibility may be modified without departing from the spirit and scope of the present invention when it is desired to have different sized curved bore diameters in combination with different radius curved bores. Therefore the principal invention is intended to apply to a wide variety of sizes and configurations of DETM as well as to apply to different operating radiuses.

The relationships between balancing the load, the forces and the masses occur in conjunction with the transfer and the constraining of the drilling energy and the net action reaction forces between the energy source and the working tip in this application. This work which is done by the present invention, the DETM for transferring drilling energy between an energy source and a working tip, will be expressed herein as a combination of balances to equal function. Therefor the function is expressed in terms of balance and balance can be expressed in terms of how the mass of the load cells relate one with respect to the other. The mass of these load cells is expressed, one load cell with respect to the other, in terms of vector force patterns. The vector force pattern can be expressed, each with respect to the others, with regard to the center of mass defined as being carried by both the load groups and by being carried by each individual wire. The center of mass of each load cell and each individual wire can be expressed, each with respect to the others, regarding their relative position in the overall transfer member. The relative position relates to the load cells and the individual wires, each with respect to the others, in terms of a moment arm leverage position in the overall transfer member. The leverage position of each load cell or each individual wire will be expressed, each with respect to the others, regarding a moment leverage advantage or disadvantage. Each moment lever, each with respect to the other, takes a relative position in the DETM and has a different force impact relative to that position in the transfer member. These moment levers relate to the way in which the present invention is manufactured. These moment levers comprise a center of mass with which each is balanced with respect to the others in properties of tensile, rotation, excursion, pitch, pivot angle, and operating pitch excursion, resulting in increased overall fatigue life.

More specifically to the balancing of the vector force load cells in terms of mass to function of the present invention of the 1×19+5+7 preferred embodiment, there are certain balances in relationship by ratio and percentage which make up the necessary balance to function characteristics which make this preferred embodiment work. These balancing ratios and percentages can be expressed generally in two primary load cells, three secondary load cells and four tertiary load cells balanced each with respect to the other and balanced with respect to function and having one central mandrel wire.

Within each of the primary, secondary, and tertiary balances the specific balancing to function relationships of percentage and ratio relate to the linear cross section, the cross sectional area, the volume, the mass, the vector slope or pitch, the load sharing, the operating excursion and the work priority done. Each of these parameters with respect to the other balance to a functional output. The balances to function expressed in terms of ratios and percentages have a different work responsibility priority at different times in the different work zone areas during a tight-radius curved bore drilling apparatus operation. The function/work priority positions in combination with the proper positioning of the land flats, the fulcrum angles, the strand deformation and the other parameters defined in this manufacturing processes of making the preferred embodiment all combine together to operate in this preferred embodiment. The two primary respective net force balances to function comprise balancing the 1×19 tensile center axial load bearing section of the transfer member with the outer shear torque carrying +5+7 wraps. The +5+7 wraps comprise just slightly greater than 50% of the overall linear cross section of the DETM. The balance to function ratio is measured in linear cross section between the two primary balances present in that the inner tensile compressor longitudinally laid 1×19 center core is approximately 10% less in linear cross section than the +5+7 outer helical torque rotational shear carrying wraps. Thus, in linear cross section the inner tensile is 10% less than the outer torque and conversely the outer torque is approximately 10% greater in linear cross section than the inner tensile. In effect we are balancing two primary load cells to a functional output.

With respect to cross sectional area regarding the overall DETM in the context of balancing the two primary load cell functions are farther apart in numerical value and with respect to relationship. When comparing the linear cross section of the two primary load cell balances to the cross sectional area balancing, the percentage ratios are more divergent. For example the load cell comprising the inner cross sectional area is approximately 44.6% in cross sectional area with respect to the outer torque carrying sectional area. Conversely the outer torque carrying cross sectional area of the overall DETM is approximately 224% greater load carrying cross sectional area. This means that the outer cross sectional area is about 2.24 times greater than the inner cross sectional area as related to central axial strength and the inner central axial strength portion of the transfer member is 2.2 times smaller than the outer torque carrying cross sectional area. It is important to remember that in balancing the two primary load cells of inner to outer, outer to inner, tensile to torque, torque to tensile, linear to helical, helical to linear, compressor to extensor, extensor to compressor, that these ratios and percentage balances exist and that they are important to the operational function of the transfer member when balancing these percentages and ratios each with respect to function and function with respect to balance. The cross sectional area of the inner tensile withstanding 1×19 central core of the preferred embodiment comprises 30.87% of the total cross sectional area of the DETM. The cross sectional area of the outer helical torque rotational carrying load is approximately 69% of the total cross sectional area. In relating the linear cross section to the cross sectional area between the two primary load cells which have been balanced to function, i.e. the 1×19 balanced with respect to function to the +5+7, it is important to note that there is only substantially a 10% difference in linear cross section but in cross sectional area the difference grows substantially to a difference of generally 224%. This plays an important role in how the vector forces are balanced in terms of slope-mass; with respect to the moment levers relative to the different positions in the transfer member and how this plays out differently and assists in the overall balancing of forces received regarding balance to function. When the transfer members are balanced to function the balance is expressed in terms of the different mass/slope/tensile relationships, each with respect to the other. In order to understand the mass, the volume of the different load bearing work cells of the transfer member are examined. The volume is expressed per a given height of transfer member or a given length of transfer member or a given lay of transfer member respective to a given diameter of transfer member. For academic purposes, as the preferred embodiment of the 1×19+5+7 is balanced to function, an example of the present invention i.e. the continuous congruent construction of transfer member is expressed with respect to height. This is expressed for academic purposes only to convey the general balances in relationships and ratios in a form that is easier to understand and of course the balances and numbers and ratios adjust and go up or down as the relationship of the length to the diameter is changed.

It is also important in looking at the volume of space allocated between the different work load bearing cells of the transfer member as each relate with respect to the others when arriving at a balance to equal function, set of percentages and ratios. In an example where the height in a straight position acting has a cylinder the volume of space occupied by the 1×19 inner tensile wraps is approximately ⅓ that of the volume of the outer torque +5+7 wraps, conversely the outer torque +5+7 wraps is approximately 3 times in volume overall of the space occupied by the 1×19 center linear tensile wraps. As expressed in terms of percentage the 1×19 occupies a volume that is approximately 33% with respect to outer torque work load bearing section and conversely the outer torque work load bearing section is approximately 353% with respect to volume of the center linear 1×19 core. The 1×19 center core volume is approximately 25% with respect to the total volume of the transfer member and the outer torque carrying +5+7 comprises approximately 75% of the total volume of the entire transfer member. As said in another way, the volume of the 1×19 linear tensile wrap comprises about ¼ of the volume with respect to the overall volume of the transfer member and the +5+7 outer torque carrying wraps comprise ¾ths of the volume with respect to the total volume of the entire transfer member. Conversely the outer torque carrying wraps comprise ¾ths of the volume with respect to the entire volume of the transfer member with respect to the 1×19 inner tensile comprising ¼th of the volume with respect to the total volume of the entire member. It is important to understand these relationships percentages and ratios each with respect to each other in combination with the cross sectional area percentage and ratios each with respect to the other and the linear cross section and ratios each with respect to the other to comprehend the magnitude of the major differences of the seemingly small variabilities when trying to understand the impact of the differences of the wire sizes, i.e. when understanding the differences of impact and importance of a 0.0045 inch 0.065 inch and 0.006 inch diameter wire, each laid with respect to each other, having a different leverage, in different operating work load cell positions in a 0.045 inch diameter DETM. When looking at the characteristics of these seemingly similar wires having seemingly small variation in diameter in terms of linear cross section, cross sectional area volume of allocated space within a transfer member and massive wire when making a balance to function transfer member in this application, it becomes apparent that the seemingly small minor differences in variances between the wire sizes translates directly into major performance differences each with respect to the other when these wire sizes are translated into a constrainment of work load energy received to energy performance work load performance output and are brought into the spatial and mechanical relationships involved in the complexities of transferring energy between an energy source and a working tip in a tight radius curved bore drill application, have a plurality of working zone positions.

In evaluating the balance as expressed in terms of mass and understanding the overall implication of putting together each work load zone cell it becomes important to understand the mass relationships between the two primary, three secondary and four tertiary work load cells. Again the ratios and percentages of mass are balanced to a function, together with the slope and leverage. Again the seemingly small apparent differences in wire size each with respect to the other of the approximate 0.0045 inch, the 0.065 inch and the 0.006 inch wires when expressed in mass by percentage and ratio each with respect to the other again show a dramatic difference each with respect to the other. Therefor from an operational point of view these major differences in percentage and ratios as expressed each with respect to the other are stacked up one on top of the other with respect to volume cross sectional area, mass, slope and leverage into wire, per work load cell each with respect to the other. Therefor the balances and force stack ups and stack downs in expressing balance and mass to function in a DETM for drilling around tight radius curved bores demonstrates that minor variations in wire size in different wraps translate functionally into major differences in balancing the receipt of work load energy percentage and ratio as expressed each with respect to the other. It is important to note that the manufacturing techniques and stress relief killing the spring temper embodied in the wire from the manufacturing process, along with matching up the land flats to create fulcrum pivot points at the center of the flats with respect to operational pitch excursion, and obtaining the proper functional work load relationships with respect to force and balance to function combine the central makeup of the present invention and comprise the subject matter of this patent application with respect to the 1×19+5+7 preferred embodiment.

Once again when evaluating the balance to function requirements of a DETM as in the present invention for the applications of drilling a tight radiused curved bore, the ratio and percentage of mass balance between the work load functional cells of the transfer member are important each with respect to the other and must be conveyed each with respect to the other. The work load priority of the two primary, three secondary and four tertiary work load cells slidably shift and change linearly with respect to each other along the DETM as a portion of the transfer member translates slidably incrementally and linearly into and out of a curvilinear operating position. The balances in force and mass to function of this single congruent transfer member construction successfully trade off and shift the work load priorities between the work load cells in the application of a drilling a tight radius curve bore.

The volume of wire per work load cell group is also expressed in balancing percentages and ratios to function. Again for academic purposes of expressing the construction of the present invention the ratios and percentages as expressed herein relate to a DETM wherein the height is a given. This is for academic purposes only in expressing each relationship with respect to the other of this single congruent construction. It is well understood that, as the length of lay or height and diameter requirements for DETM are selected and different radiuses are desired and are increased for any particular application, the volumes and masses expressed in this application will increase and decrease in proportional relationship to the finally selected lay or height. Therefor it is understood that the ratios and percentages of the load cell relationships expressed each with respect to the others in the two primary, three secondary and four tertiary work load cell relationships, will be adjusted up or down as the desired curved drill hole is adjusted and the length is adjusted for the specific application identified. The inner 1×19 construction comprising the central core portion of the transfer member comprises approximately 41.6% of total mass. Conversely the +5+7 outer helical torque shear carrying portion of the transfer member is approximately 57.3% of the total mass. Therefor we are balancing in relationship one with respect to the other an inner tensile axial load bearing portion comprising 41.6% mass with respect to an outer shear helical torque carrying wrap comprising 57.3% of total mass. Therefor 41.6% of the total mass carrying the inner tensile linear compressor axial strength is shared by 19 individual wire member units and is balanced with respect to a 57.3% total mass being load shared by 12 individual wire member units for transmission of the outer torque helical shear rotation of the transfer member. The dramatic differences between a 41.6% inner radius with respect to a 57.3% outer stack ratio up with a greater than 2.3 times the sums of the mechanical moment arm leverage differences between the inner tensile and the outer torque add up to major difference values in work load cell masses that balance the forces to function with a tight radius curved drilling application.

With respect to the sum of the individual volume mass balance between load cells with respect to three secondary load cell balances to function, the balance to function is evaluated by identifying the 1×19 center as previously identified under the true primary load balance comparison. However, the +5 right lay and the +7 left lay of the outer torque carrying wraps are broken down by their respective load cell wire mass volume numbers to further understand the relationships between the load cells and how they operate in drilling a tight radius curved bore. This is also important in understanding the differences in ratio and percentage so that again the seemingly small differences of the cross sectional diameters of the individual 0.0045 0.0065 and 0.006 wires may be translated into function in that the differences in these small diameter variations translate operationally into major balance function parameters. As previously mentioned the mass comprising the 1×19 center core comprises substantially a mass of 41.6% of the total DETM mass. Therefor 41.6% of the total DETM mass is allocated in the 1×19 center inner tensile axial compressor portion of the transfer member and is shared by 19 individual transfer member units. The +5 right hand lay comprises a wrap of five 5.0065 diameter individual transfer members. The +5 right lay wires comprise 25.1% of total DETM mass. Therefor we have a mass of 25.1 in a +5 right lay wire diameters of 0.0065 providing the right lay interlock of the shear helical rotation to the outer wrap. The +7 left hand lay comprises the outermost wrap of 7 individual unit transfer members. This mass is approximately 32.26% of the total DETM mass. The left hand lay +7 and the right hand lay +5 create an opposing interlocking configuration. Therefor the +5 right lay, comprising 25.1% of the total mass, interlocks operationally with the +7 left hand lay comprising 32.26% of the total mass. Conversely the +7 left hand lay, comprising 32.26% of the total mass, tightens down interlocks against the +5 right hand lay comprising 25.1% of the total mass, which wants to expand against the left hand lay.

When evaluating more specific parameters of the DETM which includes locking, vector force, helical pitch and vector slope, it becomes necessary to look into the DETM as having four tertiary work load cell units. Again the 1×19+5+7 preferred embodiment is comprised of one mandrel wire with six right lay wrapped around that, plus 12 left lay wrapped around that, plus 5 right lay wrapped around that, plus 7 left lay wrapped around that. Again when balancing to function, it is important to look at the mass that comprises each of the five total work load cells. Again in this example wherein the height or lay or length of the DETM is a given diameter the following numbers show the mass relationships which comprise the transfer member.

Again it is understood that for the purposes of expressing the differences in ratio and percentage of balance to function of the different work load cells of a DETM for the purposes of this application have been described in association with a DETM which has a height that is approximately twice its diameter. It is understood that the specific mathematical numerical value may be adjusted up or down to any given length according to the length of the transfer member that is desired. This adjustment, mathematically up or down, may be made with respect to the DETM having percentage and ratio relationships, the work load cells each with respect to the others and this is based upon the selection criteria for the particular curved bore drilling apparatus.

In further balancing the work load cells between a +6 right +12 left +5 right and +7 left construction of a DETM, the helical pitch angle or the slope at which each group of unit members are laid is a factor. For example when balancing the aforementioned percentage ratio relationships between the two primary load cell groups of the inner 1×19 and the outer +5+7, the helical pitch angle of the +6 right and the +12 left making up the 1×19 each are longitudinally laid more axially to the parallel center axis of the DETM at approximately 12°. Therefor we have a 12° laid 6 right lay wires cross wrapped in the opposite direction of a 12° laid 12 left hand wires. This long lay pitch is responsible for comprising the axial tensile inner strength that is required by the 1×19 inner core. The +5+7 outer torque carrying wraps are laid conversely at steeper helical pitches that are responsible for transmitting the torque shear carrying characteristics of the transfer member. The +5 right hand lay wrap is laid approximately at a range of 60°–68°. The +7 left hand lay opposing wrap is laid at approximately 68°–72°. The balance between the inner 1×19, having an axial load to the balance of the +5+7 helical torque load, is directly proportional to the 12° axial lay of the inner and the approximate 60°–70° pitch lay of the outer. The ratio of the slope of the 12° axial longitudinal lay of the +6 right and the +6 12 presents approximately a 3.5–4 times longitudinal to perpendicular in terms of lay. The +5+7 approximate pitch angle ranging from 60°–72° comprises approximately a ½–2 times the helical steepness ratio relative to the longitudinal lay. These differences in helical slope and pitch of the inner to the outer wraps combine to assist the individual unit wires in their respective load cells to be balanced to function and to comprise a life cycle that is substantially greater than the prior art.

Again it is important that the characteristics of slope, helical pitch, lay, volume and mass are balanced by load cell working groups such that balance is equal to function. It is also important to note that the exact controlling of small diameter wires ranging in sizes of 0.0045–0.0065 are difficult to control. This means that in the manufacturing process, small gaps may occur between wraps. It is important to note that, especially in the portion of the DETM which slidably translates increasingly and decreasingly into and out of the curve drilling position, the forces are so great that the gaps between the wires are eliminated. Therefor the manufacturing pitch angles are adjusted by operational pitch angles in the section of the flex shaft that operates in the tight radius. As the gaps are eliminated and the wires operate buttressed side-to-side in all directions the gaps are taken up and the pitch angles are slightly increased in proportion to the amount of space gapping that was present in the wires from manufacturing and prior operation. Therefor it is consistent to say that the operational pitch of the wires in the DETM and the operational pitch angle excursion that occurs in the portion of the DETM that operates in the curve are adjusted by the operation of the transfer member. Again these factors combined with stress relieving the manufactured flexible shaft such that slope and the pitch angles are as close to the adjusted operational pitch angles as possible, add to the life cycle of the transfer member. In addition, stress relieving and killing the spring temper in the wires for manufacture at precisely the operational pitches laid at manufacturing, produces a flexible shaft that is manufactured with pitches and lays that, when put into operation, have only minor adjustments to make to go from the manufactured pitch to the operational pitch. The pitch excursion or the operational pitch excursion that occurs upon rotation of the transfer member is thus as close to the center of mass kill position as possible. This reduces the amount of cold work forming operation in that the molecular structure of the wires are tempered and killed in close relationship to the adjusted operational pitch excursion.

It is understood that the foregoing description and accompanying drawings have been given by way of illustration and example. It is also to be understood that changes in form of the several parts, substitution of equivalent elements and arrangement of parts which will be readily apparent to one skilled in the art, are contemplated as within the scope of the present invention, which is limited only by the claims which follow.

What is claimed is:

1. A flexible drilling energy transfer member comprising;
an inner core load cell comprising a first plurality of strands sized and laid at helical angles sufficient for transmitting predetermined tensile and compression loads under rotary drilling pressure, and
an outer wrap load cell comprising a second plurality of strands sized and laid at helical angles sufficient for transmitting predetermined torque loads under rotary drilling pressure,
the force fields and mass distribution of said load cells being balanced in function such that said first load cell structurally supports said second load cell against destruction by axially directed forces and said second load cell structurally supports said first load cell against destruction by rotationally directed torque forces and maintains longitudinal support therefor.

2. A multi strand flexible drilling energy transfer member for tight radius rotary drilling comprising;
a core construction composed of a first plurality of strands comprising a first load cell for transmitting tensile and compression loads while under rotary drilling pressure,
said first plurality of strands being generally axially directed and laid at flat helical angles,
an outer wrap construction surrounding said core and composed of a second plurality of strands comprising a second load cell for transmitting rotational torque loads while under rotary drilling pressure,
said second plurality of strands being generally circumferentially directed and laid at steep helical angles,
the force fields and mass distribution of said first and second load cells being balanced in fuction such that said first load cell structurally supports said second load cell against destruction by axially directed forces and said second load cell structurally supports said first load cell against destruction by rotationally directed torque forces and maintains longitudinal support therefor.

3. The drilling energy transfer member of claim 2 wherein;
said first plurality of strands are sized and laid at helical angles sufficient for transmitting predetermined tensile and compression loads under rotary drilling pressure, and
said second plurality of strands are sized and laid at helical angles sufficient for transmitting predetermined torque loads under rotary drilling pressure.

4. The drilling energy transfer member of claim 3 wherein;
said fist plurality of strands comprise a single strand mandrel and first and second oppositely directed inner helical strand wraps laid thereon at flat helical angles forming an interlocking configuration for transmitting axial loads.

5. The drilling energy transfer member of claim 4 wherein;
said second plurality of strands comprises first and second oppositely directed outer helical stand wraps laid at steep helical angles forming an interlocking configuration for transmitting torque loads.

6. The drilling energy transfer member of claim 3 wherein;
said drilling energy transfer member has a given total mass and said first and second load cells comprise primary load cells,
the mass of said first load cell constitutes approximately 41.6% of the total mass, and
the mass of said second load cell comprises the balance of the total mass.

7. The drilling energy transfer member of claim 6 wherein;
said second load cell comprises separate radially successive first and second reversely wound helical torque wraps, each wrap including a plurality of stands,
said first torque wrap comprising a middle torque wrap constituting approximately 25.1% of the total mass, and
said second torque wrap comprising an outer torque wrap constituting approximately 32.2% of the total mass.

8. The drilling energy transfer member of claim 7 wherein;
said first load cell comprises a central mandrel strand and inner and outer reversely wound helical core wraps, each wrap including a plurality of strands,
said inner core wrap constitutes 12.6% of the total mass,
said outer core wrap constitutes 27% of the total mass, and
said mandrel strand constitutes 1.8% of the total mass.

9. The drilling energy transfer member of claim 8 wherein;
said middle torque wrap comprises five right hand laid strands,
said outer torque wrap comprises seven left hand laid strands,
said inner core wrap comprises six right hand laid strands, and
said outer core wrap comprises twelve right hand laid strands.

10. The drilling energy transfer member of claim 5 where in;
said first and second inner helical strand wraps are laid at 10°–15° helical angles, and
said first and second outer helical strand wraps are laid at 60°–68° and 68°–72° helical angles respectively.

11. The drilling energy transfer member of claim 8 wherein;
said inner core and outer core wraps are laid at 10°–15° helical angles, and
said middle and outer torque wraps are laid at 60°–68° and 68°–72° helical angles respectively.

12. A flexible drilling energy transfer member comprising;
a core load cell for transmitting axial tensile and compression loads during drilling pressure, and an outer wrap torque transmitting load cell,
said core load cell including a single strand mandrel, a first six strand right hand laid wrap and a second twelve strand left hand laid wrap,
said outer wrap load cell including a first five strand outer wrap laid on said twelve strand wrap in a right hand direction and a second seven strand outer wrap laid on said five strand wrap in a left hand direction.

13. The drilling energy transfer member of claim 12 wherein;
   the overall diameter of said drilling energy transfer member is 0.045 inches,
   said six strand and said twelve strand wraps are laid at helical angles of 10°–15°,
   said five strand wrap is laid at helical angles of 60°–68°, and
   said seven strand wrap is laid at helical angles of 68°–72°.

14. The drilling energy transfer member of claim 13 wherein;
   said mandrel, said six strand wrap and said twelve strand wrap comprise 0.0045 inch diameter wires,
   said five strand wrap comprises 0.0065 inch diameter wires, and
   said seven strand wrap comprises 0.006 inch diameter wires.

15. A rigid construction connecting a cutter head to the terminal end of a flexible rotary shaft having a given diameter, said shaft including a core load cell and a separate outer load cell for transmitting axial and torque loads respectively, said structure comprising;
   a hollow cylindrical stem on said cutter head,
   said hollow stem having an internal diameter sized to snugly receive a portion of the terminal end of said shaft; and
   at least one fused weld extending through the body of said stem into the center area of said shaft,
   whereby the relationship and stability between said load cells is maintained during rotation thereof.

16. A rigid construction connecting a cutter head to the terminal end of a flexible rotary shaft having a given diameter comprising;
   a hollow cylindrical stem on said cutter head,
   said hollow stem having an internal diameter sized to snugly receive a portion of the terminal end of said shaft; and
   a plurality of radially directed fused areas spaced circumferentially about the wall of said stem,
   said fused areas extending from the outer surface of the stem to the center of said shaft.

17. A rigid construction for connecting a cutter head to the end of a flexible rotary shaft having a given diameter comprising;
   a hollow cylindrical stem on said cutter head,
   said stem having an internal diameter sized to snugly receive a portion of the terminal end of said shaft,
   a shoulder on said cutter head located immediately adjacent the bottom of said hollow stem, and
   at least one fused weld extending obliquely through said shoulder into the center area of said shaft.

18. A rigid construction for connecting a cutter head to the terminal end of a flexible rotary shaft having a given diameter comprising;
   a stem on said cutter head having a diameter equal to the diameter of said shaft and adapted to abuttingly engage the terminal end thereof,
   a hollow cylindrical sleeve having an internal diameter sized to receive said shaft and said stem thereon with a snug fit, and
   at least one fused weld extending through the body of said sleeve into the center area of the abutting end faces of said stem and said shaft.

19. The construction of claim 18 wherein said fused weld comprises a plurality of radially directed fused areas spaced circumferentially about the wall of said sleeve.

20. The construction of claim 18 wherein said fused weld is located adjacent one end of said sleeve adjacent said cutter head.

21. The construction of claim 19 including;
   a rigid collar attached to the outside of said sleeve for contacting the drill grid of a drilling apparatus.

22. A flexible rotary shaft for transferring energy to a working member comprising in combination;
   an inner load cell,
   an outer load cell concentric with said inner load cell,
   said inner load cell comprising substantially longitudinally laid load bearing units for carrying longitudinally directed loads and resisting longitudinal deformation, and
   said outer load cell comprising helically laid load bearing units for transferring rotary shear torque energy.

23. A flexible drilling energy transfer member comprising in combination:
   an inner load cell comprising a core with substantially longitudinally laid load bearing units being wrapped substantially linearly for carrying longitudinally directed loads and resisting longitudinal deformation, and
   an outer load cell concentric with said inner load cell and comprising helically wrapped torque load bearing cell units for transferring rotary shear torque drilling energy.

24. A multi-strand flexible drilling energy transfer member having two primary functionally balanced load cells comprising;
   an inner load cell having an inner cross sectional area and an outer load cell having an outer cross sectional area, said inner cross sectional area being approximately 25% with respect to the total cross sectional area and approximately 66.7% less than the outer cross sectional area,
   the volume of said inner load cell being approximately 25% with respect to the total volume and approximately 66.7% less than the volume of the outer load cell,
   the mass of said inner load cell being approximately 41.6% with respect to the total mass and approximately 20.7% less than the mass of the outer load cell,
   the strands of said inner and outer load cells being laid with predetermined helical slopes wherein the net slope vectors of the inner load cell is 204% with respect to the net slope vectors of the outer load cell, whereby the total combined net sloping force is balanced to function,
   said inner and outer load cells each having a work priority wherein the inner load cell primarily functions in balance with the outer load cell to withstand and resist linear deformation and the outer load cell primarily functions to transfer and constrain drilling energy in helical torque and shear.

25. The drilling energy transfer member of claim 24 wherein said inner load cell has a net center of mass leverage value of 3× and said outer load cell has a net center of mass leverage value of 7×.

26. The drilling energy transfer member of claim 24 wherein said two primary load cells are functionally balanced for load bearing primarily tensile to torque and torque to tensile, linear to rotary and rotary to linear.

27. The drilling energy transfer member of claim 25 wherein said two primary load cells are functionally balanced for load bearing primarily tensile to torque and torque to tensile, linear to rotary and rotary to linear.

28. A multi-strand flexible drilling energy transfer member comprising;
- inner and outer helically laid concentric load cells,
- said load cells being functionally balanced with respect to net vector slope, net mass, net volume, net cross sectional area and net load cell center of mass leverage values, such that the inner load cell resists linear elongation and deformation and the outer load cell provides the balance of transfer of torque forces.

29. The drilling energy transfer member of claim 28 wherein said inner and outer load cells are functionally balanced for load bearing primarily tensile to torque and torque to tensile, linear to rotary and rotary to linear.

30. The drilling energy transfer member of claim 22 wherein;
- said inner load cell is laid longitudinally to the axis of the drilling energy transfer member,
- said outer load cell comprising a pair of cross linked opposing units for the transmission of helical shear load.

31. The drilling energy transfer member of claim 22 including;
- an energy source,
- a working tip,
- said drilling energy transfer member being connected between said energy source and said working tip to transfer drilling energy therebetween,
- said inner load cell being laid and wrapped to withstand extension and compression forces,
- said outer load cell comprising a pair of cross linked interlocking cell units for transferring and constraining helical shear torque rotary forces between said energy source and said working tip.

32. A drilling energy transfer member for transferring drilling energy between an energy source and a working tip comprising;
- an inner tensile load cell comprising substantially longitudinally laid load bearing units for carrying longitudinally directed loads and resisting longitudinal deformation, and
- an outer cross linked pair of stranded load cells,
- the outer cross linked load cells being stranded and laid for transmission of rotary torque shear forces between the energy source and the working tip,
- the net slope vector forces of the cross linked load cells being balanced in function and equilibrium to provide counter opposing interlocking constraint.

33. The drilling energy transfer member of claim 24 wherein;
- said outer load cell comprises counter opposing right and left laid load cell units, said outer load cell comprising the balance of the cross sectional area, volume and mass of the drilling energy transfer member,
- said inner load cell comprising a net vector slope approximately 148% to the total, directed 88% toward tensile load, and
- said outer load units having a net vector slope directed 430% toward torque load.

34. The drilling energy transfer member of claim 33 including;
- an energy source,
- a working tip,
- said drilling energy transfer member being connected between said energy source and said working tip to transfer drilling energy therebetween.

35. The drilling energy transfer member of claim 31 wherein;
- the diameter of said drilling energy transfer member is one half the diameter of said working tip and configured to operate in the curved bore formed thereby.

36. The drilling energy transfer member of claim 35 wherein said drilling energy transfer member is configured to transfer drilling energy along a curved bore radius of approximately 0.25 inches and to rotate and reciprocate therein.

37. The drilling energy transfer member of claim 36 wherein;
- the cubic load cell units space volume changes upon rotation throughout the curve bore path, the helical pitch excursion and the shifting thereof being made in proportion to the radius of operation of the drilling energy transfer member to the outside diameter thereof,
- the force field distribution being so high as to close gaps between the load cell units in the curved path causing side-by-side contact of the load cell units upon excursion in reaction to rotation and translation within the curved path.

38. Curved bore drilling apparatus comprising in combination;
- a rotary drive means;
- a cutter tip;
- a drill shaft adapted for connection to said rotary drive means, said drill shaft means having a distal flexible drilling energy transfer member with said cutter tip attached thereto,
- mounting means supporting said drill shaft for movement in a rectilinear path, and
- guide means to guide said flexible drilling energy transfer member and said cutter tip from said rectilinear path along a curved path to form said curved bore,
- said flexible drilling energy transfer member comprising an inner load cell and a concentric outer load cell,
- said inner load cell comprising substantially longitudinally laid load bearing units for transmitting tensile forces, and
- said outer load cell comprising helically laid load bearing units for transferring rotary torque drilling energy,
- the force fields and mass distribution of said load cells being balanced in function such that the inner load cell structurally supports said outer load cell against destruction by axially directed forces and said outer load cell structurally supports said inner load cell against destruction by rotationally directed torque forces and maintains longitudinal support therefor.

39. The drilling apparatus of claim 38 wherein;
- said inner and outer load cells comprise helically wrapped cross linked load cell units.

40. The drilling apparatus of claim 39 wherein;
- said inner load cell includes a single strand mandrel and said load cell units comprise a plurality of helically laid strands,
- the diameter of said drilling energy transfer member being approximately 0.045 inches and said curved bore has a radius of approximately 0.25 inches.

41. The drilling energy transfer member of claim 23 wherein;

said inner load cell includes;

a single strand mandrel unit for linear support, a right hand wound six strand load sharing cell unit, and a left hand wound twelve strand load sharing cell unit, the load cell units of said inner load cell resisting substantially linear deforming loads.

42. The drilling energy transfer member of claim 41 wherein said outer load cell includes;

a right hand wound five strand load sharing cell unit, and a left hand wound seven strand load sharing cell unit, the load cell units of said outer load cell resisting shear torque loads, said inner and outer load cells being balanced in function such that the inner load cell structurally supports said outer load cell against destruction by axially directed forces and said outer load cell structurally supports said inner load cell against destruction by rotationally directed torque forces and maintains longitudinal support therefor.

43. The drilling energy transfer member of claim 42 wherein;

the strands of said load cell units comprise wires drawn and cold worked to a desired material temper and wrapped in layers having a cold work effect and maintaining a spring load, the drilling energy transfer member being heat tempered as stranded to stress relieve said strands close to operating excursion pitch angles.

44. The drilling energy transfer member of claim 43 wherein;

the spring temper is killed close to operating excursion positions so that land flats on said strands provide pivotal fulcrums as the strands move and shift in reaction to change in run mode patterns as the drilling energy transfer member moves through a curved path.

45. The drilling energy transfer member according to claim 1 wherein said transfer member includes;

terminal ends for connection to a rotary power source and a working member respectively, and a thermally fused connection between said load cells on at least one of said terminal ends, whereby the relationship and stability between said load cells is maintained during rotation thereof.

46. The drilling energy transfer member according to claim 45 wherein said thermally fused connection comprises;

at least one fused weld extending through the body of said outer wrap load cell into the body of said inner core load cell.

47. The drilling energy transfer member according to claim 45 wherein said thermally fused connection comprises;

a plurality of radially directed fused welds spaced circumferentially about the wall of said member, said fused welds extending through the body of said outer wrap load cell into the body of said inner core load cell.

* * * * *

UNITED STATES PATENT AND TRADEMARK OFFICE
CERTIFICATE OF CORRECTION

PATENT NO. : 6,267,679 B1
DATED : July 31, 2001
INVENTOR(S) : Jack W. Romano

It is certified that error appears in the above-identified patent and that said Letters Patent is hereby corrected as shown below:

<u>Column 23,</u>
Line 67, change "stand" to -- strand --.

<u>Column 24,</u>
Line 17, change "stands" to -- strands --.

Signed and Sealed this

Sixteenth Day of April, 2002

Attest:

JAMES E. ROGAN
*Attesting Officer*     *Director of the United States Patent and Trademark Office*